United States Patent [19]

Takasaki et al.

[11] Patent Number: 4,529,696
[45] Date of Patent: Jul. 16, 1985

[54] PROCESS FOR LIQUEFACTION OF STARCH

[75] Inventors: Yoshiyuki Takasaki, Tsukuba; Yoshimasa Takahara, Ibaraki; Chikashi Izumi, Kitami; Atsushi Mori, Kitami; Masahiko Nishiguchi, Kitami; Masaru Yamada, Kitami, all of Japan

[73] Assignee: Agency of Industrial Science & Technology, Ministry of International Trade & Industry, Tokyo, Japan

[21] Appl. No.: 509,586

[22] Filed: Jun. 30, 1983

Related U.S. Application Data

[62] Division of Ser. No. 309,099, Oct. 6, 1981, Pat. No. 4,410,368.

[30] Foreign Application Priority Data

Oct. 11, 1980 [JP] Japan .................. 55-142174

[51] Int. Cl.$^3$ .................. C12P 19/14; C12P 19/20
[52] U.S. Cl. .................. 435/99; 435/96
[58] Field of Search .................. 435/95, 96, 99

[56] References Cited

U.S. PATENT DOCUMENTS

| | | | |
|---|---|---|---|
| 2,004,135 | 6/1935 | Rothrock | 568/861 |
| 3,378,462 | 4/1968 | Denault | 435/99 X |
| 3,492,203 | 1/1970 | Mitsuhashi | 435/95 |
| 3,709,788 | 1/1973 | Best | 435/99 X |
| 3,853,706 | 12/1974 | Armbruster | 435/99 |
| 3,928,135 | 12/1975 | Milner | 435/99 |
| 4,014,743 | 3/1977 | Black | 435/99 |
| 4,298,400 | 11/1981 | Armbruster | 435/99 X |

*Primary Examiner*—Lionel M. Shapiro
*Attorney, Agent, or Firm*—Oblon, Fisher, Spivak, McClelland & Maier

[57] ABSTRACT

A liquid starch solution suitable for saccharification into a maltose-containing product is obtained by suspending starch in water, adding to the starch suspension a heat resistant α-amylase and a carbonate, adjusting the resultant mixture to a pH value in the range of from 7.5 to 8.0, and thermally treating the resultant starch milk while repressing possible hydrolysis of starch molecules.

4 Claims, No Drawings

PROCESS FOR LIQUEFACTION OF STARCH

This is a division of application Ser. No. 309,099, filed Oct. 6, 1981, now U.S. Pat. No. 4,410,368, issued Oct. 18, 1983.

BACKGROUND OF THE INVENTION

This invention relates to a process for the liquefaction of starch in the manufacture of a maltose-containing substance by the saccharification of a liquid starch solution.

One known method heretofore adopted for the manufacture of a maltose-containing substance from starch has comprised the steps of saccharifying a liquid starch solution with a saccharifying enzyme, optionally treating the saccharified starch solution further with $\alpha$-amylase added thereto, refining the saccharified solution through filtration, a treatment with an activated carbon and a treatment with an ion-exchange resin, and concentrating the refined solution thereby producing a maltose-containing solution. When necessary, this solution was further concentrated and dried to produce powdered maltose. More recently, there has been proposed a method for producing maltose in high yields by treating the liquid starch solution with $\beta$-amylase and $\alpha$-1,6-glucosidase (U.S. Pat. No. 3,992,261).

The methods heretofore proposed for the liquefaction of starch include (i) a method which involves heating starch milk at a temperature in the range of from 150° to 165° C., with the pH value of the starch milk adjusted, or not adjusted, in the range of from 5 to 6 in advance, (ii) a method which involves maintaining starch milk in the presence of an acid added thereto at 120° C. for a short period of time, (iii) a method which involves adjusting the pH value of starch in the range of from 5 to 6, adding $\alpha$-amylase to the starch milk, heating the resultant mixture at a temperature in the range of from 80° to 95° C. for 1 to 30 minutes and thereafter maintaining the mixture at a temperature in the range of from 120° to 140° C. for 5 to 20 minutes thereby inactivating the $\alpha$-amylase, and (iv) a method which, subsequently to the procedure of the method (iii) terminated by the step of the inactivation of $\alpha$-amylase, further involves cooling the heated mixture to 90° C., thereafter adding $\alpha$-amylase again to the mixture, and effecting secondary liquefaction, for example.

In the methods of liquefaction described above, even when the adjustment of the pH value of starch milk is completely omitted, the starch for saccharification to be used on a commercial scale contains some amount of an acidic substance. When this starch is suspended in water, the resultant suspension has its pH value gradually fall with elapse of time and eventually reaches a point of exhibiting acidity. In the case of corn starch, for example, the $SO_2$ which has been used in the course of the production of corn starch persists in the corn starch and constitutes itself one main cause for the drop of the pH value of the corn starch during the liquefaction and saccharification of the starch. In the case of sweet potato starch, the starch is recovered first in the form of starch milk from the sweet potatoes and the starch milk thus recovered is subjected in its unmodified form to starch saccharification or subjected to drying by dehydration. In any event, in some if not all of the lots, the starch may be immersed in water. During such prolonged standing under water, the starch may possibly undergo fermentation and produce organic acids such as lactic acid and butyric acid, and thereafter entrain such organic acids. In this respect, the commercial-grade starch is different from the refined starch of the reagent grade. Worse still, in the case of a method which involves preparatory adjustment of the pH value in the range of from 5.5 to 6.0 or a method which effects the liquefaction by addition of an acid, the pH value continues to drop with the gradual progress of liquefaction and reaches a very low level by the time that the liquefaction is completed. This adverse situation is generally corrected by readjusting the reaction system to the optimum pH value for the saccharifying enzyme either before or during the saccharification.

As the source for starch, aerially grown starches such as corn, wheat, and sago palm and underground grown starches such as potato, sweet potato, and cassava are available. It is known that generally the aerially grown starches contain sparingly soluble starches in higher percentages than the underground grown starches and, therefore, undergo liquefaction with greater difficulty. According to the passages found on pages 123–129 and pages 314–319 of "Agricultural and Biological Chemistry" (Agr. Biol. Chem.), Vol. 32, 1968, insoluble starch is defined as what is obtained by liquefying a given starch with an ample amount of bacterial $\alpha$-amylase, collecting the residual insoluble component by centrifugal separation, and assaying the insoluble component by the anthrone method. According to the test results reported, the insoluble starch content is about 230 mg % in corn starch, more than 200 mg % in wheat starch, about 9 mg % in potato starch, and about 25 mg % in sweet potato starch. (Here, "mg %" is used to signify the weight (in mg) of insoluble starch per 100 g of a given starch.)

An effort made to obtain from a starch having a high insoluble starch content a liquid starch solution having a low hydrolysis ratio (such as less than DE 2, for example) necessary for the production of a saccharified product of a high maltose content (such as not less than 80% of solids, for example) results in production of a cloudy white liquid starch solution with residual unliquefied starch particles in suspension. Consequently, the solution after the saccharification is difficult to refine. On the other hand, an effort to obtain a liquid starch solution free from such a suspension as mentioned above results in production of a solution involving excessive hydrolysis of starch. The liquid starch solution, when saccharified, does not give a product of improved maltose purity. In the case of the aforementioned known method of liquefaction, the pH value is low at the end of the liquefaction. In the case of the saccharifying enzyme to be used in the present invention, since the optimum pH value falls in the range of from 6 to 8, it becomes frequently necessary to have the pH value of the liquid starch solution readjusted prior to and during the reaction of saccharification. The necessity for the pH value readjustment has proved to be a problem from the standpoint of prevention of contamination and of operational efficiency.

SUMMARY OF THE INVENTION

An object of this invention is to provide a process for the liquefaction of starch for the manufacture of a substance of saccharification with high maltose purity.

Another object of this invention is to provide a process for the liquefaction of starch having a high insoluble starch content, suitable for the manufacture of a maltose-containing substance having high maltose purity.

To accomplish the object described above according to the present invention, there is provided a process for the liquefaction of starch, which comprises the steps of suspending the starch in water, adding to the resultant suspension a heat resistant α-amylase and a carbonate, adjusting the starting pH value in the range of from 7.5 to 8.0, and subjecting the resultant starch milk to thermal treatment.

The liquid starch solution obtained as described above has a pH value in the neighborhood of 6.0 to 6.5. Thus, it can be put, directly without any pH adjustment, to manufacture of maltose by the addition thereto of a saccharifying enzyme.

The other objects and characteristics of the present invention will become apparent from the further disclosure of the invention to be made below.

DESCRIPTION OF PREFERRED EMBODIMENT

The inventors have discovered a microorganism capable of producing β-amylase and α-1,6-glucosidase simultaneously and have succeeded in producing maltose by use of the complex enzyme (U.S. Pat. No. 3,992,261). The inventors have further continued various experiments and studies with a view to developing a method for obtaining products of saccharification having higher maltose purity by use of the complex enzymes mentioned above. They have consequently found that products of saccharification having higher maltose contents can be obtained by converting starch into a liquid starch solution of low hydrolysis ratio by an improved process of liquefaction. This invention has issued from this knowledge.

For a given starch to be saccharified with a saccharifying enzyme, the starch particles must be dissolved in water. The starch particles are formed by the crystallization of amylose and amylopectin both of very high molecular weights sharing long glucose chains and united to each other through an α-1,4 bond and an α-1,6 bond. No substantial hydrolysis of this starch is obtained by merely adding water thereto. In the added water, the starch remains unaltered in its original form of particles. In this state, an enzyme can act on the starch particles only with difficulty. To facilitate the action of the enzyme upon the starch, the starch is liquefied by the steps of first suspending the starch in water to produce starch milk, then rupturing the starch particles with heat and physical force, and further dissolving the crystalline micelles of the aforementioned glucose chains. Although this liquefaction can be carried out rather easily on starch milk having a starch content of not more than 5% for example, the commercial operation generally requires the starch content of the starch milk to be at least 15%. Unfortunately, the rise of viscosity of the starch during the hydrolysis is accelerated in proportion as the starch content of the starch milk increases. When the viscosity is increased, the uniform heating of starch becomes proportionally difficult and the retrogradation of the hydrolyzed starch (recrystallization of starch molecules) occurs more readily. To prevent the viscosity from excessively rising and to preclude the retrogradation completely, α-amylase or an acid is added to the starch so as to sever suitably the long glucose chains of starch molecules (hydrolysis). When the degree of this severance of glucose chains is increased, namely the hydrolysis ratio of starch molecules is heightened, the yields of such fragmentary products as glucose and maltotriose increase during the severance of glucose chains into maltose units with the β-amylase in the subsequent treatment for saccharification. By effecting the liquefaction of starch with the hydrolysis of starch particles limited to the minimum (thus ensuring production of a liquid starch solution of repressed hydrolysis ratio), thereto, the subsequent treatment for saccharification is enabled to afford a product of saccharification having a high maltose content.

The first step in the method of this invention is to prepare starch milk by stirring starch in water to obtain a starch suspension (generally to a solids concentration of 15 to 30% by weight), adding a carbonate of calcium, sodium, or potassium to the suspension and, at the same time, adjusting the pH value of the suspension to a level in the range of from 7.5 to 8.0, and further adding heat resistant α-amylase (capable of functioning at temperatures above 100° C.) thereto. The amount of the heat resistant α-amylase to be added is desired to be in the range of from 0.05 to 0.3% based on the solid starch content. The amount of the aforementioned carbonate to be added is desired to fall in the range of from 0.5 to 1.5% based on the solid starch content. The carbonate is used herein to serve as a buffer for protecting the starch suspension against the pH drop during the liquefaction and saccharification. Amoung other carbonates, calcium carbonate proves particularly advantageous because it dissolves itself in proportion to the acidity of the suspension and aids in neutralizing the acid and, consequently, provides a buffering function for a long time.

When slaked lime or calcium hydroxide is added to the starch milk to adjust the pH value thereof in the range of from 7.5 to 8.0, this calcium hydroxide lends itself to repressing the decomposition of starch molecules by an acid, enhancing the swell and rupture of starch particles during the subsequent steps of gelatinization and liquefaction of starch as by a thermal treatment, and giving rise to an amply homogeneous, clear liquefied starch having a low hydrolysis ratio. Compared with the conventional method which effects the liquefaction of starch with the pH value of starch milk maintained in the range of from 5 to 6 or in a more acidic range, the method of the present invention, when applied to liquefaction of a starch having a high insoluble starch content like corn starch or a starch containing $SO_2$ or an organic acid in a high concentration, enhances the swell and rupture of insoluble starch particles, represses otherwise inevitable decomposition of starch molecules by an acid, and consequently facilitates production of a uniformly liquefied and sparingly hydrolyzed starch. The expression "uniformly liquefied and sparingly hydrolyzed starch" used here means a liquefied starch which exhibits not merely a low DE level but also a low iodine number and has no suspended solid particles. For example, this expression describes a liquid starch solution which has a starch concentration of 25%, a DE level in the neighborhood of 2, and an iodine number of not more than 0.8 and which is free from suspended particles.

The term "DE" as used herein means the content of reducing sugar, expressed in the amount of glucose, relative to the solid starch content. The iodine number is determined by the procedure which comprises mixing 1 ml of a given sample with 2 ml of 1N-NaOH, allowing the resultant mixture to stand for 30 minutes, stirring this mixture with 5 ml of distilled water and 2 ml of 1N-H$_2$SO$_4$, collecting 1-ml portion of the resultant mixed solution, mixing the portion with 1 ml of 1N-H$_2$SO$_4$, 0.1 ml of 0.1N-iodine solution, and 7.9 ml of distilled water thereby producing a colored mixture, and testing the mixture for absorbance at 610 m$\mu$ with a photometer using a 10-mm glass cell. The zero adjustment of the photometer is made by using the mixture prepared by following the procedure described above, except that distilled water is used in the place of the sample. The reading of absorbance on the photometer is reported as the iodine number. This measurement is based on the degree of the blue color which is generated when iodine combines with starch molecules. In the case of liquid starch solutions prepared from one and the same starch by different methods of liquefaction, therefore, their iodine numbers may vary while their DE levels are identical. When the iodine number exceeds 0.8, there ensues a disadvantage that the high molecular weight dextrin arising from the treatment using $\alpha$-amylase after the step of saccharification is not easily removed and, consequently, the subsequent treatments with activated carbon and ion-exchange resin are difficult to perform and the final product inevitably contains suspended particles and fails to acquire the high maltose purity expected.

The liquefaction of starch which suits the manufacture of maltose, therefore, should be governed not merely by the DE level but also by the iodine number of the starch solution and the freedom of the starch solution from suspended particles.

The starch milk prepared as described above is then liquefied by a thermal treatment (including the treatment with $\alpha$-amylase) which is performed batchwise or continuously.

Batchwise liquefaction:

The starch milk is placed in a tank and stirred and, at the same time, heated to 100° to 110° C. with blown steam. When this elevation of temperature takes too much time, the starch tends to undergo retrogradation. When the temperature elevation occurs too quickly, the volume of heat applied to the starch becomes insufficient. Although the time for this temperature elevation is variable with the speed of stirring, it is generally desired to fall in the range of from 5 to 15 minutes. After the starch milk has reached the temperature level mentioned above, it is retained at this level for three to five minutes and acted upon by $\alpha$-amylase to effect the primary gelation (accompanied by the primary liquefaction by the $\alpha$-amylase). Subsequently, the starch milk is heated to 140° to 150° C. and retained at this level for 15 to 40 minutes to swell and rupture starch particles (secondary gelation). At this time, the $\alpha$-amylase is no longer functioning because it has already been inactivated. Then, the resultant starch solution is suddenly cooled to 95° to 100° C. and retained at this temperature for 5 to 30 minutes in the presence of 0.05 to 0.3% (based on the solid starch content) of the heat resistant $\alpha$-amylase added thereto, to undergo the second liquefaction. The decomposition of starch molecules is accelerated and the growth of maltose purity in the subsequent saccharification is curbed in proportion as the time of the secondary liquefaction is increased. To produce maltose with purity of 80% or over, therefore, it is necessary that the time for the secondary liquefaction should be limited to the allowable minimum. The disappearance of the cloudiness from the secondarily liquefied starch solution may well be regarded as a safe sign for completion of the liquefaction. Now, the liquid starch solution is heated to 135° to 145° C. and retained at this temperature for five minutes so as to ensure perfect inactivation of $\alpha$-amylase and, at the same time, completion of the liquefaction of starch. It is subsequently cooled suddenly to 50° to 55° C. and forwarded to the step of saccharification.

Continuous liquefaction:

(1) The batchwise liquefaction described above is carried out in a tank. In contrast, the continuous liquefaction is carried out by continuously feeding the starch milk through pines under the conditions of temperatures and retention times as involved in the aforementioned batchwise liquefaction. In this case, for the purpose of stirring and heating of the solution involved, there may be used a device such as the known onlater which is provided with a jacket adapted to permit passage of steam for heat application and a scraper rotated within a cylindrical housing.

(2) The procedure described in (1) above is followed, except that the temperature of the starch milk is elevated virtually instantaneously to 140° to 150° C. by using the known jet cooker instead of the onlater mentioned above. Optionally, the temperature elevation to 135° to 145° C. for the inactivation of $\alpha$-amylase after the secondary liquefaction may be effected by use of the jet cooker.

In the continuous liquefaction described above, the prepared starch milk is heated instantaneously to 140° to 150° C. Since the blown steam imparts powerful stirring and shear strength to the starch milk, the action of $\alpha$-amylase upon the starch milk which lasts only momentarily brings about ample liquefaction of the starch.

The liquid starch solution which is obtained by the batchwise or continuous liquefaction is free from the cloudiness. This fact implies that the liquefaction of starch has been effected thoroughly. (The solution is cloudy white when the liquefaction of starch is imperfect.) At the end of the liquefaction, the pH value of the solution falls to the neighborhood of 6.0 to 6.5. This range is embraced by the optimum pH range, 6 to 8, for the saccharifying enzyme to be used in the present invention. Thus, the liquid starch solution requires absolutely no pH adjustment such as is generally performed prior to the treatment for saccharification.

The method of this invention is highly effective because the initial pH value of the starch milk for liquefaction is maintained at a high level of from 7.5 to 8.0 to render the starch milk amply resistant to pH variation and also because the liquefaction is enabled to proceed at a high temperature owing to the use of heat resistant $\alpha$-amylase. Besides, even starch which has a high insoluble starch content can be liquefied amply enough (not excessively) by performing the high-temperature liquefaction in two separate steps. This liquid starch solution is ideal for the saccharification by use of the saccharifying enzyme specified by the present invention. The saccharification, accordingly, produces maltose of high purity.

The liquid starch solution which has been suddenly cooled to 50° to 55° C. as described above can be immediately subjected to saccharification by the addition thereto of the aforementioned saccharifying enzyme. For the purpose of this saccharification, the complex enzyme of $\beta$-amylase and $\alpha$-1,6-glucosidase which is produced by Bacillus cereus var. mycoides (ATCC 31102) disclosed in U.S. Pat. No. 3,992,261 and deposited with A.T.C.C. on Dec. 26, 1974 by one of the inventors can be advantageously used.

The bacteria mentioned above can produce the composite enzyme by cultivation in a solid or liquid culture medium in ordinary use. As a solid culture medium, a culture medium of wheat bran is usable. The seed culture is inoculated to this culture medium and cultured. After the culture, the produced composite enzyme is extracted with water to afford a coarse composite enzyme. This coarse composite enzyme may be put to use in its unmodified form as a saccharifying enzyme. Otherwise, it may be suitably concentrated and refined before the use.

As a liquid culture medium, a culture medium which contains starch, a partial starch hydrolyzate such as dextrin, and a carbon source such as maltose is generally usable. Other culture media usable herein include those which contain peptone, casein, meat extract, yeast extract, corn steep liquor, soybean, and soybean cake as nitrogen sources and further contain inorganic nitrogen sources, phosphates, magnesium salts, and calcium salts as supplementary components.

The culture is carried out at a temperature in the range of from 20°0 to 40° C. for one to three days under continued aeration. Since the pH value of the culture medium fluctuates between 5.5 and 9.5 during the culture, it is desirable to take a measure for controlling the pH value of the culture medium in the range of from 6 to 8 during the culture.

By the time the culture is completed, both $\beta$-amylase and $\alpha$-1,6-glucosidase have departed from the cells and settled within the culture broth. The culture broth is filtered to remove the cells. The filtrate is concentrated and then sedimented in an organic solvent such as acetone, ethanol, methanol, or iso-propanol. The sedimented composite enzyme may be further concentrated as by the precipitation with a salting agent such as ammonium sulfate. In the case of the precipitation by use of ammonium sulfate, 60 to 100% of $\beta$-amylase and $\alpha$-1,6-glucosidase in a mixed state can be recovered in the form of a precipitate saturated to about 70 to 75%.

The filtrate, the concentrate, the sediment in the organic solvent, and the precipitate by salting which occur at the various stages invariably contain $\beta$-amylase and $\alpha$-1,6-glucosidase and, therefore, can be used as sources for the saccharifying enzyme for the production of maltose from starch.

The two components of the composite enzyme which is obtained by the culture described above, namely, $\beta$-amylase and $\alpha$-1,6-glucosidase, are both SH-enzymes in nature. When cystein, sodium thioglycolate, etc. are added to the composite enzyme during or after its preparation, therefore, the enzymatic activity of the composite enzyme can be enhanced.

When the composite enzyme so produced as to acquire an activity ratio of $\beta$-amylase to $\alpha$-1,6-glucosidase in the range of from about 10:1 to about 20:1 is used in an amount of 300 to 600 units of $\beta$-amylase activity (15 to 60 units of $\alpha$-1,6-glucosidase activity) per g of solid starch to saccharify the liquid starch solution, the saccharification continued for 20 to 45 hours will produce a maltose solution of 75 to 85% purity.

The saccharified solution contains some amount of a high molecular weight dextrin. This high molecular weight dextrin has a possibility of adversely affecting the subsequent filtration and the treatments with an activated carbon and an ion-exchange resin. To preclude this trouble, $\alpha$-amylase is added to the saccharified solution at the end of the saccharification reaction to decompose the high molecular weight dextrin. This treatment with $\alpha$-amylase should by all means be performed after the saccharification reaction has been completed. This treatment with $\alpha$-amylase, if performed before the completion of the saccharification reaction, will have the adverse effect of lowering the maltose purity. For use in this treatment, any commercially available $\alpha$-amylase will suffice so far as it satisfies the requirement that it should function at the temperature and pH conditions involved in the aforementioned saccharification reaction and should not be resistant to heat. In the treatment with $\alpha$-amylase, the time at which the solution produces no white suspension in an 80% aqueous alcohol solution and produces a white suspension in an 85% aqueous alcohol solution may be safely taken as the end point of the treatment. When the liquefaction treatment has been adequately performed in accordance with the method of this invention, the treatment with $\alpha$-amylase performed at 55° C. comes to completion in 10 to 30 minutes. If the liquefaction has been incomplete, the treatment with $\alpha$-amylase must be performed for a long time and the treatment itself is not so effective as expected. When the end point of the treatment with $\alpha$-amylase is reached, the pH value of the solution is lowered to 4.0 by addition of oxalic acid. Then the solution is heated at 80° C. for 20 minutes to inactivate $\alpha$-amylase and the composite enzyme. The use of oxalic acid in this case has an advantage that calcium ions present in the solution can be removed in the form of a precipitate of calcium oxalate. Optionally hydrochloric acid may be used for the pH adjustment. In this case, however, the calcium ions persist in the solution and exert a greater load on the ion-exchange resin.

The resultant solution is concentrated to a solids concentration of 50% (Bx 50°), or not concentrated, and subjected to decolorization with an activated carbon and purification with an ion-exchange resin, and again concentrated to the level of about Bx 70° to afford a liquid sugar. Otherwise, this liquid sugar may be further concentrated, solidified, pulverized, and dried to afford powdered maltose. Consequently, there is obtained maltose of 80 to 90% purity. This maltose is assayed for sugar composition by well-known gas chromatography, with the result reported in terms of solids content (Bx) in percent. As the internal standard, there is used sucrose. The analysis obtained of the maltose by the gas chromatography is substantially equal to the analysis obtained by the high-speed liquid chromatography.

The high-purity maltose obtained as described above has a glucose content of less than 0.1% and, therefore, is sparingly susceptible to coloration by glucose. As a quality sweetener of mild taste, this maltose can be used in foodstuffs. It can also be used advantageously as the raw material for maltose preparations for intravenous administration to patients of diabetes.

Now, the present invention will be described more specifically below with reference to examples.

EXAMPLE 1

In a sterilized culture medium containing 3.0% of milk casein, 0.5% of liquefied starch, 0.5% of ammonium dihydrogenphosphate, 0.3% of dipotassium hydrogenphosphate, 0.1% of magnesium sulfate, 1.0% of rice bran, 0.2% of polysodium acrylate, 0.0147% of $Ca^{++}$, 0.00009% of $Mn^{++}$, 0.00135% of $Fe^{++}$, and 0.00124% of $Cu^{++}$, a seed culture of Bacillus cereus var. mycoides (ATCC 31102) was inoculated and cultured at 30° C. under aerated stirring. After completion of the culture, the enzyme produced was refined and concentrated by ultrafiltration, precipitated by salting, and subjected to filtration, recovery, and drying. The enzyme thus obtained showed 66,000 units/g of β-amylase activity and 6,600 units/g of α-1,6-glucosidase activity.

Separately, 66 kg of corn starch (having a water content of 13%) was mixed with water to a total volume of 400 l and then mixed with 600 g of calcium carbonate. The pH value of the resultant mixture was adjusted to 7.8 by addition of slaked lime. To the starch milk thus prepared, a heat resistant α-amylase (produced by Novo Industri A/S, Denmark and marketed under trademark designation of "Termamyl 60L") was added in an amount of 0.1% based on the solid starch content. While under agitation, the starch milk was heated to 100° C. over a period of 10 minutes, retained at this temperature for 3 minutes, and further heated to about 145° C., retained at this temperature for 15 minutes, and then cooled by flushing to 100° C. With 0.1% of the aforementioned α-amylase added again thereto, the starch milk was stirred at 100° C. for 7 minutes to be liquefied, then heated to 145° C., retained at this temperature for about 5 minutes to inactivate the α-amylase. At this point, the liquid starch solution showed a DE level of about 2 and an iodine number of about 0.45. Then, the hot liquid starch solution was suddenly cooled to 100° C. by flushing, then further cooled in a coil and a jacket provided in the tank to 55° C. While the solution was kept at 55° C., the composite enzyme obtained as described above was added in an amount such as to give a β-amylase content of 300 units and an α-1,6-glucosidase content of 30 units respectively per g of the solid starch content. The saccharification of the starch which ensued was completed in 45 hours. The resultant saccharified solution was composed (based on solids) of 0.05% of glucose, 82.51% of maltose, 6.32% of maltotriose, and 11.12% of other components. The saccharified solution was treated with 0.1%, based on the solid starch content, of an α-amylase (produced by Daiwa Kasei Co., Ltd., Japan and marketed under trademark designation of "Kleistase $L_1$") at 55° C. for 20 minutes. The solids of the mixture after this treatment were composed of 0.06% of glucose, 84.71% of maltose, 6.73% of maltotriose, and 8.50% of other components.

The resultant solution was adjusted to pH 4.0 by addition of 1M oxalic acid, and heated at 80° C. for 20 minutes to inactivate the β-amylase, α-1,6-glucosidase, and α-amylase. The solution was filtered with a filter press. The filtrate was concentrated at 50° C. to Bx 50°. The concentrate was decolored with a granular activated carbon (produced by Kuraray Chemicals Limited, Japan and marketed under trademark designation of "Kuraraycoal GLC"), and then refined sequentially through a column packed with a strongly acidic decationizing resin (produced by Mitsubishi Chemical Industry Co., Ltd., Japan and marketed under trademark designation of "Diaion SK-1B"), through a column packed with a weakly basic deanionizing resin (similarly marketed under trademark designation of "Diaion WA-30") and through a mixed resin column packed with a strongly acidic decationizing resin (similarly marketed under trademark designation of "Diaion PK-216") and a strongly basic deanionizing resin (similarly marketed under trademark designation of "Diaion PA-406"), filtered, and concentrated to Bx 85°. The concentrate was combined with 5% of seed sugar, mixed with a kneader, divided into small fractions, left standing at room temperature to be solidified and aged (for four days), pulverized, and dried. Consequently, there was obtained 60.6 kg of powdered maltose. By gas chromatography, this maltose was found to be composed (based on solids content) of 0.05% of glucose, 87.74% of maltose, 7.64% of maltotriose, and 4.57% of other components. The water content of this powdered maltose was found to be 6%.

For the purpose of comparison, the same starch was liquefied by following the procedure described above, except that the amount of calcium carbonate added was changed to 60 g, the pH value of the starch milk was changed to 6.0, and the temperature of heating each after the first and second treatments with α-amylase was changed to 130° C.

The liquid starch solution consequently obtained showed a pH value of 5.2, a DE level of 1.7, and an iodine number of more than 1.0. This liquid starch solution was adjusted to pH 6.5 with caustic soda. It was then subjected to a saccharification treatment with the composite enzyme under the same conditions as described above for 65 hours. Whenever the pH value fell below 6.0, the solution was readjusted to pH 6.5.

The resultant saccharified solution was composed of 0.07% of glucose, 66.16% of maltose, 2.91% of maltotriose, and 30.86% of other components. In the solution, a fair proportion of the starch remained in an unaltered form.

EXAMPLE 2

The procedure of Example 1 was repeated, except that the amount of the composite enzyme used was doubled to give a β-amylase content of 600 units and an α-1,6-glucosidase content of 60 units respectively per g of solid starch content and the duration of saccharification was shortened to 20 hours. The resultant powdered maltose was composed (based on solids content) of 88.94% of maltose, 6.88% of maltotriose, and 4.18% of other components, with no detectable dextrose.

EXAMPLE 3

A starch milk having a solids content of 20% was prepared by using potato starch and 0.1 weight by volume % of calcium carbonate and 0.1%, based on the solid starch content, of α-amylase (Termamyl 60L). This starch milk was heated to 100° C. over a period of 8 minutes, retained at this temperature for 3 minutes, then heated to 145° C., and retained at this temperature for 15 minutes. It was then cooled to 100° C. by flushing and, with 0.1% of the same α-amylase added thereto, retained at 100° C. for 7 minutes. Then, this solution was heated to 135° C. and retained at this temperature for 5 minutes. The resultant liquid starch solution showed a pH value of 6.55, a DE level of 2.5 and an iodine number of 0.7, and no white cloudiness appeared in this solution.

This liquid starch solution was cooled to 55° C. To the cooled solution, the composite enzyme was added in an amount such as to give a β-amylase content of 600 units and an α-1,6-glucosidase content of 100 units respectively per g of solid starch content. The ensuing saccharification was allowed to proceed for 20 hours. The resultant saccharified solution was composed, based on the solids content, of 0.1% of glucose, 87.1% of maltose, 4.7% of maltotriose, and 8.1% of other components. The solution had a pH value of 6.40. Virtually no residual starch was found in the solution.

EXAMPLE 4

This example represents a continuous liquefaction of starch by use of a jet cooker (made by Hydro-thermal Corp., U.S.A. and marketed under trademark designation of "Hydroheater Model BS-500"). Corn starch was suspended in water to a level of Bx 18.5°. To the aqueous suspension, a heat resistant α-amylase (Termamyl 60L) was added in an amount of 0.1% based on the solid starch content and calcium carbonate was also added in an amount of 1% based on the solid starch content. The mixture was adjusted to pH 7.9 by addition of slaked lime. Consequently, there was obtained starch milk.

This starch milk was continuously fed under pressure (about 4.5 kg/cm$^2$) with a metering pump at a flow volume of 6 l/min. into the jet cooker and, at the same time, steam was blown in under a pressure of 4.5 to 5.0 kg/cm$^2$ to elevate the temperature of the starch milk to about 145° C. The heated starch milk was passed through a retention pipe (with the inner pressure kept at 3.5 kg/cm$^2$) so as to give the starch milk a retention time of about 40 minutes. The first liquefied solution was suddenly cooled to 100° C. by flushing under atmospheric pressure. To the cooled solution, the same heat resistant α-amylase as described above was added in the same proportion. The resultant solution was passed through a retention pipe adapted so as to give the solution a retention time of about 7 minutes and effect the second liquefaction. The solution was again fed under pressure with a metering pump into the jet cooker and, at the same time, steam was blown in. It was then retained at 145° C. for 5 minutes to inactivate the α-amylase. Thereafter, the solution was suddenly cooled to about 55° C. by flushing, to complete the saccharification treatment. From this point on, the procedure of Example 1 was followed. Consequently, there was obtained a maltose-containing product having a purity of 88.35%.

What is claimed is:

1. A process for the liquefaction of starch in the manufacture of maltose by the liquefaction of starch and the subsequent saccharification of the resultant liquid starch solution with a saccharifying enzyme which optimally functions at a pH value within the range of 6 to 8 with a saccharifying enzyme, which comprises the steps of:
    (a) suspending an amount of starch in water such that it has a solids concentration of 15 to 30% by weight;
    (b) adding to said starch suspension an amount of a carbonate as a buffer and α-amylase capable of functioning even at temperatures above 100° C.;
    (c) adjusting the pH value of the suspension of step (b) within the range of 7.5 to 8.0;
    (d) heating the resultant starch containing mixture to a temperature in the range of 140° to 150° C. with pressurized vapor and retaining said heated starch suspension at said temperature from 15 to 40 minutes thereby inactivating said α-amylase and at the same time swelling and rupturing starch particles in said suspension;
    (e) rapidly cooling the resultant starch suspension to a temperature in the range of 95° to 100°;
    (f) adding to said cooled starch suspension from 0.05 to 0.3%, based on the starch content of the suspension, of α-amylase capable of functioning even at a temperature above 100° C. and retaining the mixture at said temperature of 95° to 100° C. for 5 to 30 minutes; and
    (g) heating the mixture to a temperature in the range of 135° to 145° C. and retaining the mixture at this temperature for about 5 minutes in order to inactivate said α-amylase enzyme.

2. The process of claim 1, wherein said carbonate in step (b) is a member selected from the group consisting of calcium carbonate, sodium carbonate and potassium carbonate, and wherein said carbonate is added to the starch suspension in an amount of from 0.5 to 1.5% based on the starch content of the suspension.

3. The process of claim 1, wherein aid α-amylase in step (b) is added to the suspension in an amount of from 0.05 to 0.3% based on the starch content of the suspension.

4. The process of claim 1, wherein said liquefied starch product has a DE level of about 2 and an iodine number of not more than 0.8.

* * * * *